US012446855B2

(12) United States Patent
Fuson

(10) Patent No.: US 12,446,855 B2
(45) Date of Patent: Oct. 21, 2025

(54) ERGONOMIC AND SAFE ULTRASOUND PROBE HANDLE SYSTEM AND METHOD

(71) Applicant: BON SECOURS MERCY HEALTH, INC., Cincinnati, OH (US)

(72) Inventor: Martin R. Fuson, Monroe, MI (US)

(73) Assignee: BON SECOURS MERCY HEALTH, INC., Cincinnati, OH (US)

( * ) Notice: Subject to any disclaimer, the term of this patent is extended or adjusted under 35 U.S.C. 154(b) by 303 days.

(21) Appl. No.: 18/184,296

(22) Filed: Mar. 15, 2023

(65) Prior Publication Data

US 2023/0293150 A1 Sep. 21, 2023

Related U.S. Application Data

(60) Provisional application No. 63/319,844, filed on Mar. 15, 2022.

(51) Int. Cl.
*A61B 8/00* (2006.01)

(52) U.S. Cl.
CPC .......... *A61B 8/4455* (2013.01); *A61B 8/4218* (2013.01)

(58) Field of Classification Search
CPC .................................................... A61B 8/4455
See application file for complete search history.

(56) References Cited

U.S. PATENT DOCUMENTS 5,390,661 A 2/1995 Griffith et al.
5,678,551 A 10/1997 Stevens
9,161,738 B2 10/2015 Tsung
10,159,469 B2 12/2018 Stoianovici et al.
10,368,850 B2 8/2019 Kamen et al.
10,939,955 B2 3/2021 Zarins et al.
11,045,244 B2 6/2021 Zarins et al.
2004/0002647 A1 1/2004 Desai
2007/0038112 A1 2/2007 Taylor et al.
2011/0201930 A1 8/2011 Guzman
2013/0178745 A1 7/2013 Kyle, Jr. et al.
2015/0059768 A1 3/2015 Guzman
2015/0201902 A1 7/2015 Zhu et al.
2017/0215949 A1 8/2017 Zarins et al.
2019/0090956 A1 3/2019 Franz et al.
2019/0183588 A1 6/2019 Kusumoto
2020/0008737 A1 1/2020 Lee et al.
2020/0054353 A1* 2/2020 Yun .................... A61B 18/1485
2020/0187898 A1* 6/2020 Toporek ................. A61B 8/483
2020/0237437 A1 7/2020 Gasperment et al.
2021/0290312 A1* 9/2021 Gaudreau .............. A61B 34/30

* cited by examiner

*Primary Examiner* — Rochelle D Turchen

(74) *Attorney, Agent, or Firm* — Jacob M. Ward; Ward Law Office LLC

(57) ABSTRACT

An ergonomic ultrasound handle device can include a handle body. An ergonomic ultrasound handle device can include a clamp body connected to the handle for engaging an ultrasound transducer, the clamp body including a top end and a bottom end, with a clip disposed on the top end of the clamp body for maintaining the ultrasound transducer in engagement with the handle body. A method of ergonomically controlling an ultrasound transducer can provide the ergonomic ultrasound handle device. The method can include removably attaching the handle device to the handle of an ultrasound transducer. The method can include controlling the ultrasound transducer by applying pressure and motion to the handle, whereby the handle transmits the motion and pressure to the transducer.

11 Claims, 8 Drawing Sheets

ERGONOMIC AND SAFE ULTRASOUND PROBE HANDLE SYSTEM AND METHOD

CROSS-REFERENCE TO RELATED APPLICATIONS

This application claims the benefit of U.S. Provisional Application No. 63/319,844, filed on Mar. 15, 2022. The entire disclosure of the above application is incorporated herein by reference.

FIELD

The present technology relates to ultrasound equipment. More specifically, the present technology relates to ergonomic handles for ultrasound equipment with improved user interface and safety.

Introduction

This section provides background information related to the present disclosure which is not necessarily prior art.

Medical sonography covers a broad spectrum of specialty areas including vascular, cardiac, and general (e.g., abdominal, superficial parts, gynecologic and obstetric) sonography. Because medical sonography covers such a broad array of clinical needs without the use of ionizing radiation, it has become essential in the diagnosis of many life-threatening diseases.

Though sonography is an indispensable tool, it is not without its shortcomings. For example, each year more than 80% of clinical sonographers experience musculoskeletal related pain, with up to 20% of these sonographers suffering career-ending injuries. Current research points to the poor ergonomics of ultrasound probes or transducers as a main factor in causing these work-related musculoskeletal disorders. Specifically, work-related musculoskeletal disorders, including those of the hand, wrist, shoulders, neck and back have been linked to grip effort and other ergonomic factors for those using ultrasound transducers inherent in current designs.

In tests undertaken to pinpoint the cause of these hand and wrist musculoskeletal disorders, muscle activation was quantified as an indirect measure of the grip effort required by the sonographer to perform a scan with the ultrasound transducer. Additionally, sonographers performing endocavity procedures are often poked or injured by needles or other surgical instruments during the procedure. These potential injuries can create additional potential harm to the sonographers as well as increased stress regarding this potential for harm.

Accordingly, there is a continuing need for a more ergonomic gripping assembly/handle interface between the sonographer and ultrasound transducer in order to reduce work-related musculoskeletal disorders and other injuries.

SUMMARY

In concordance with the instant disclosure, an ergonomic ultrasound gripping device/handle has surprisingly been discovered.

In one embodiment, an ergonomic ultrasound handle device can include a handle body. An ergonomic ultrasound handle device can include a clamp body connected to the handle for engaging an ultrasound transducer, the clamp body including a top end and a bottom end, with a clip disposed on the top end of the clamp body for maintaining the ultrasound transducer in engagement with the handle body.

In another embodiment, a method of ergonomically controlling an ultrasound transducer by providing the ergonomic ultrasound handle device is provided. The method can include removably attaching the handle device to the handle of an ultrasound transducer. The method can include controlling the ultrasound transducer by applying pressure and motion to the handle device, whereby the handle transmits the motion and pressure to the transducer.

The present technology enables an individual to more ergonomically and safely hold an ultrasound device. The gripping assembly/handle of the present disclosure provides for more ergonomic positioning of the user's hand relative to the ultrasound device. In other words, the device allows the user to maintain a more comfortable hand position during use of the transducer. The handle device can therefore minimize work-related musculoskeletal disorders of the user's hand and wrist. Additionally, the handle device can help to prevent needle sticks and other surgical instrument related injuries for the user, thereby creating a safer probe handle.

Additionally, the handle device allows the user of the ultrasound probe/transducer to maintain the appropriate position of the ultrasound transducer during a procedure, while not inhibiting or blocking access for a practitioner (e.g., physician, nurse, medical technician, etc.) during a procedure. The handle device allows the user to comfortably maintain the ultrasound probe/transducer in the proper orientation without impacting the practitioner's clearance and/or ability to accurately and efficiently complete the procedure. Also, as stated above, the handle device improves sonographer safety because the sonographer's hand is maintained a distance from the practitioner, wherein the likelihood of additional injuries to the sonographer are further limited.

In another embodiment, the handle device can be controlled by a robotic device. The robotic device can be used to perform an ultrasound procedure and the handle can be used to assist the robot in performing this function. Alternatively, the handle device can be used by the robot to program and develop AI within the robot's programming to calibrate or fine tune the motions and handling of endocavity scanning using ultrasound. The handle device can also include a break-away feature that allows the handle device, and accordingly the transducer, to be disengaged when the pressure being applied by the robot exceeds preset limits or the robot is malfunctioning or not appropriately providing sensing information to the human user.

One additional use of the handle device is as a teaching device. The handle device enables a teacher to assist a student using an ultrasound transducer without contacting the student's hand. In other words, the handle device allows a teacher to assist a student, that is holding the ultrasound transducer, and thus provide guidance with respect to one or more ultrasound techniques during a procedure without having to be in contact with the student.

In an exemplary embodiment, the handle device can be removably engaged to the handle of an ultrasound transducer. The handle device can be formed of a material known to those of skill in the art that is non-reactive, biocompatible, and sanitizable. In one embodiment of the present disclosure, the handle device can be specifically designed to attach to a specific ultrasound transducer. In another embodiment, the handle device is universally designed to attach to any ultrasound transducer handle.

As shown in the figures, the handle device can include at least a clamp body and a handle body. The clamp body can also include one or more clips. The clips and the handle body can be formed of the same material, including various polymers, composites, and other materials compatible with ultrasound devices, examples of which are well known to those of skill in the art. Alternatively, the clips can be formed of a different material from that of the handle body.

The clips can be shaped to engage the handle of an ultrasound transducer. The clips can be formed to allow the handle device to be removably attached to the handle of an ultrasound transducer. This engagement can enable the handle device to control the positioning of the transducer, while creating a space between the handle of the transducer and the handle device. The benefit of this engagement can be to allow the user to hold the transducer in an ergonomic position.

More specifically, the clips can be shaped to fit a specific brand of transducer. In other words, the clips have an inner surface that can be designed to be complementary or specifically mate with one or more portions of the handle shape of a specific brand of transducer. Alternatively, the clips can be formed to enable engagement with any ultrasound transducer.

The clips can be shaped to include a channel into which the handle of an ultrasound transducer is placed. The clips can include spring fit arms to engage the sides of the transducer handle and hold the transducer handle in place. The inner surface of the arms can optionally include a gripping material, texture material, or textured surface that can grippingly engage the transducer handle. Examples of such materials include, but are not limited to, an elastomer, foam, plastic, or other polymers known to those of skill in the art.

The clamp body can be removably attached to the handle body for allowing the clamp body to be removed and/or replaced. Alternatively, the clamp body can be formed as a single unit with the handle and the clips can be removably attached to the clamp body. When the clamp body is formed as a single unit with the handle, the locking mechanism is no longer a separate component of the clamp body.

Optionally, the handle device can include a locking mechanism for locking the clamp body in engagement with the handle body.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

DETAILED DESCRIPTION

Figure 1:
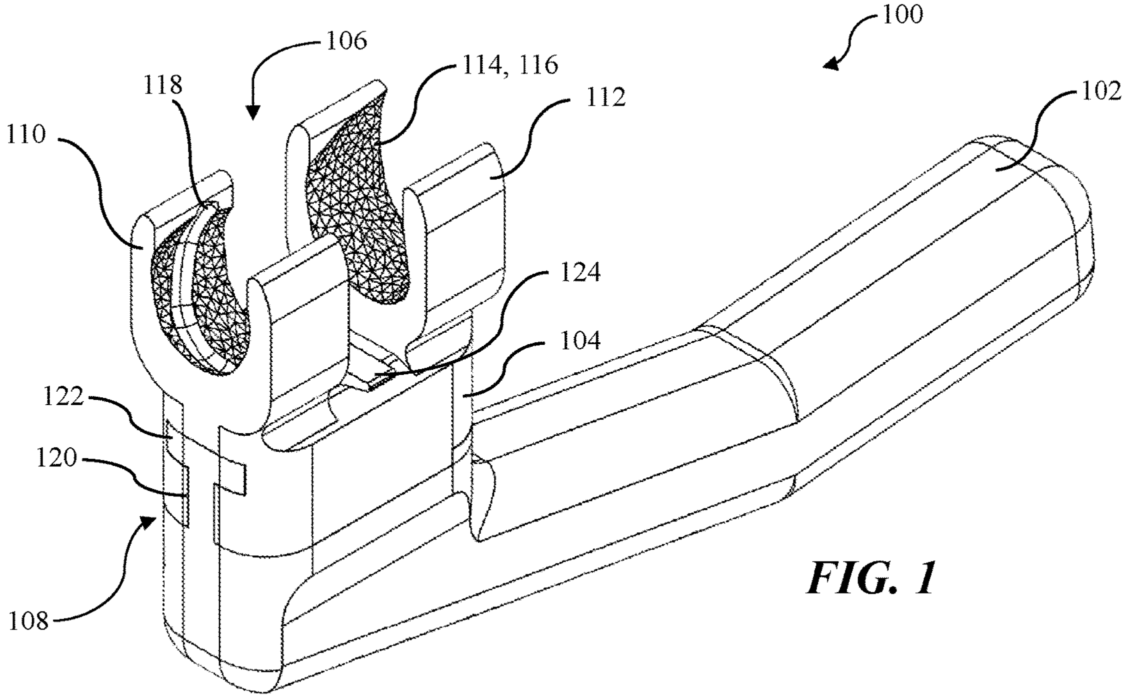
FIG. 1 is a top perspective view of an ergonomic ultrasound handle device, according to some embodiments of the present disclosure.

The following description of technology is merely exemplary in nature of the subject matter, manufacture and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that can be recited in the art, even though element D is not explicitly described as being excluded herein.

When an element or layer is referred to as being "on," "engaged to," "connected to," or "coupled to" another element or layer, it can be directly on, engaged, connected or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

FIGS. 1-9 show an ergonomic ultrasound handle device 100, according to some embodiments of the present disclosure. The present technology enables an individual to more ergonomically and safely hold an ultrasound device. The gripping assembly/handle of the present disclosure provides for a more ergonomic positioning of the user's hand relative to the ultrasound device. In other words, the device allows the user to maintain a more comfortable hand position during use of the transducer. The handle device can therefore minimize work-related musculoskeletal disorders of the user's hand and wrist. Additionally, the handle device can help to prevent needle sticks and other surgical instrument related injuries to the user, thereby creating a safer probe handle device.

Additionally, the handle device allows the user of the ultrasound probe to maintain the appropriate position of the ultrasound transducer during a procedure, while not inhibiting or blocking access for a practitioner (e.g., physician, nurse, medical technician, etc.) during a procedure. The handle device allows the user to comfortably maintain the ultrasound device in the proper orientation without impacting the practitioner's clearance and/or ability to accurately and efficiently complete the procedure. Also, as stated above, the handle device improves sonographer safety because the sonographer's hand is maintained a distance from the practitioner, wherein the likelihood of additional injuries to the sonographer are further limited.

In another embodiment, the handle device can be controlled by a robotic device. The robotic device can be used to perform an ultrasound procedure and the handle device can be used to assist the robot in performing this function. Alternatively, the handle device can be used by the robot to program and develop AI within the robot's programming to calibrate or fine tune the motions and handling of endocavity scanning using ultrasound. The handle device can also include a break-away feature that allows the handle device, and accordingly the transducer, to be disengaged when the pressure being applied by the robot exceeds preset limits or the robot is malfunctioning or not appropriately providing sensing information to the human user.

The ergonomic ultrasound handle device 100 can include a handle body 102 and a clamp body 104 connected to the handle body 102. The ergonomic ultrasound handle device 100 can be utilized for engaging an ultrasound transducer. In certain embodiments, the clamp body 104 can be formed as a single unit with the handle body 102. In other embodiments, for example as shown in FIGS. 1-2, the clamp body 104 can be removably, slidably coupled to the handle body 102.

Figure 2:
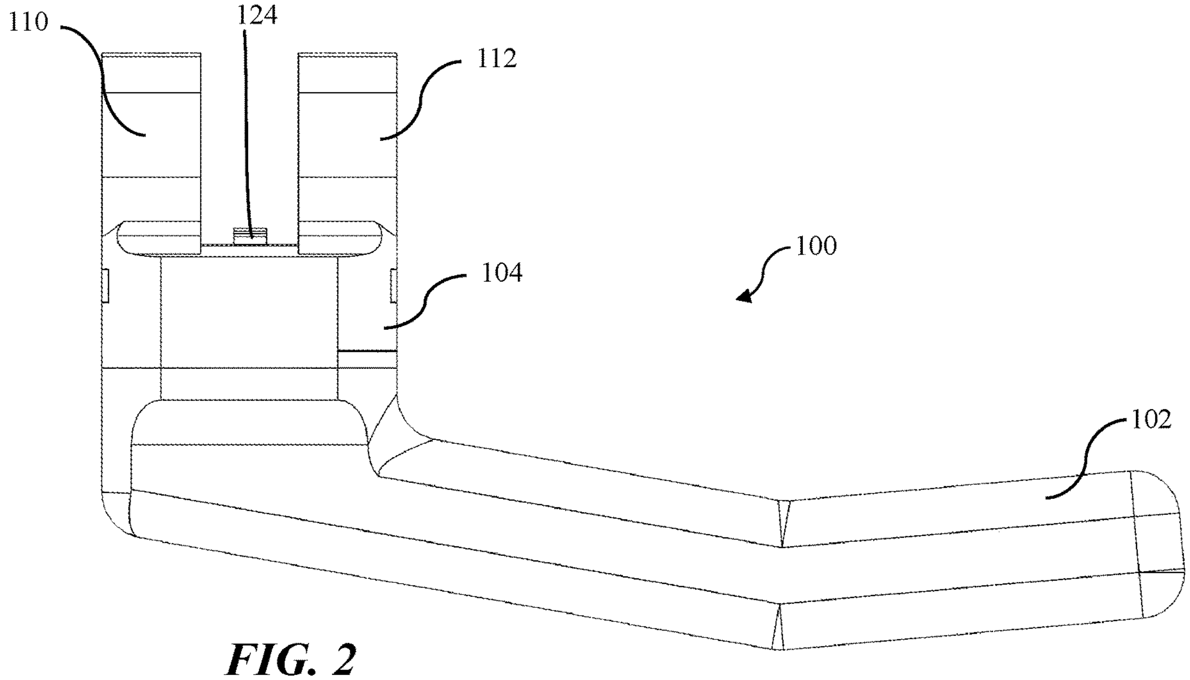
FIG. 2 is a side elevational view of the ergonomic ultrasound handle device from FIG. 1.
Figure 3:
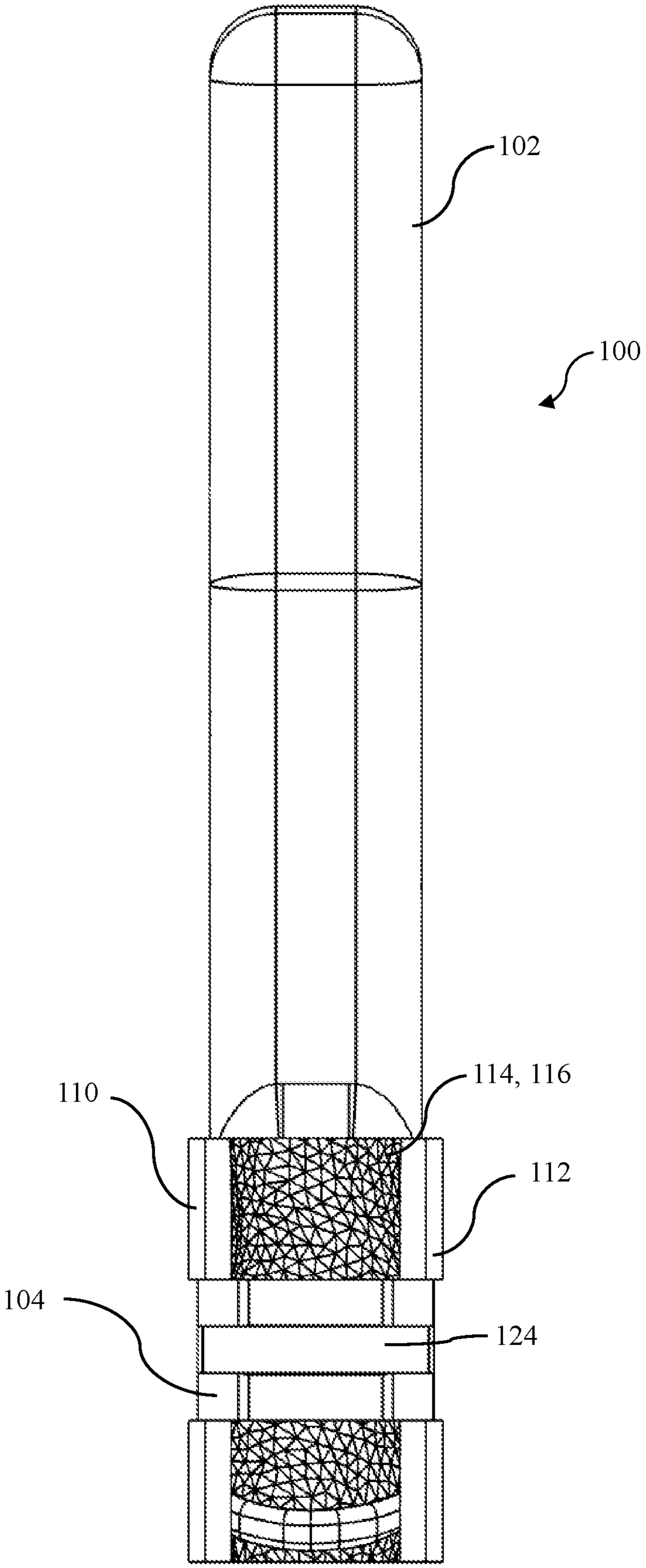
FIG. 3 is a top plan view of the ergonomic ultrasound handle device from FIG. 1.
Figure 4:
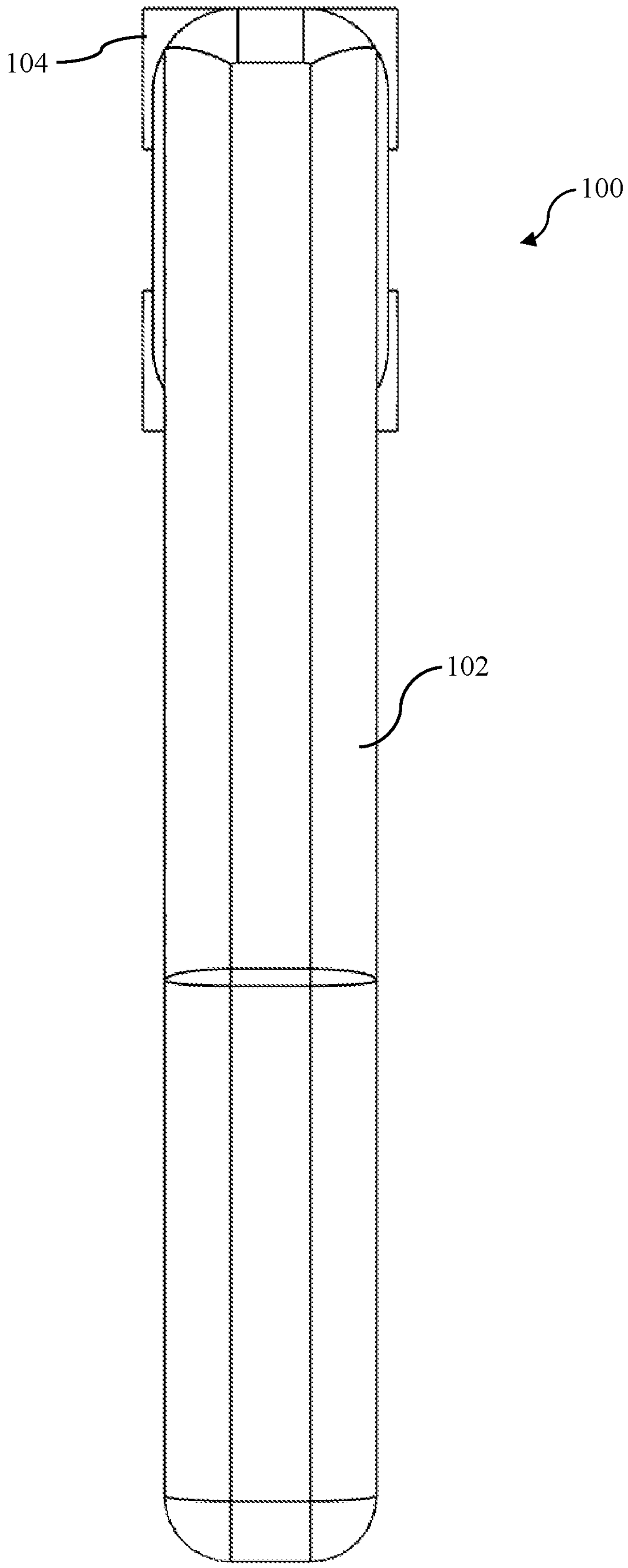
FIG. 4 is a bottom plan view of the ergonomic ultrasound handle device from FIG. 1.
Figure 5:
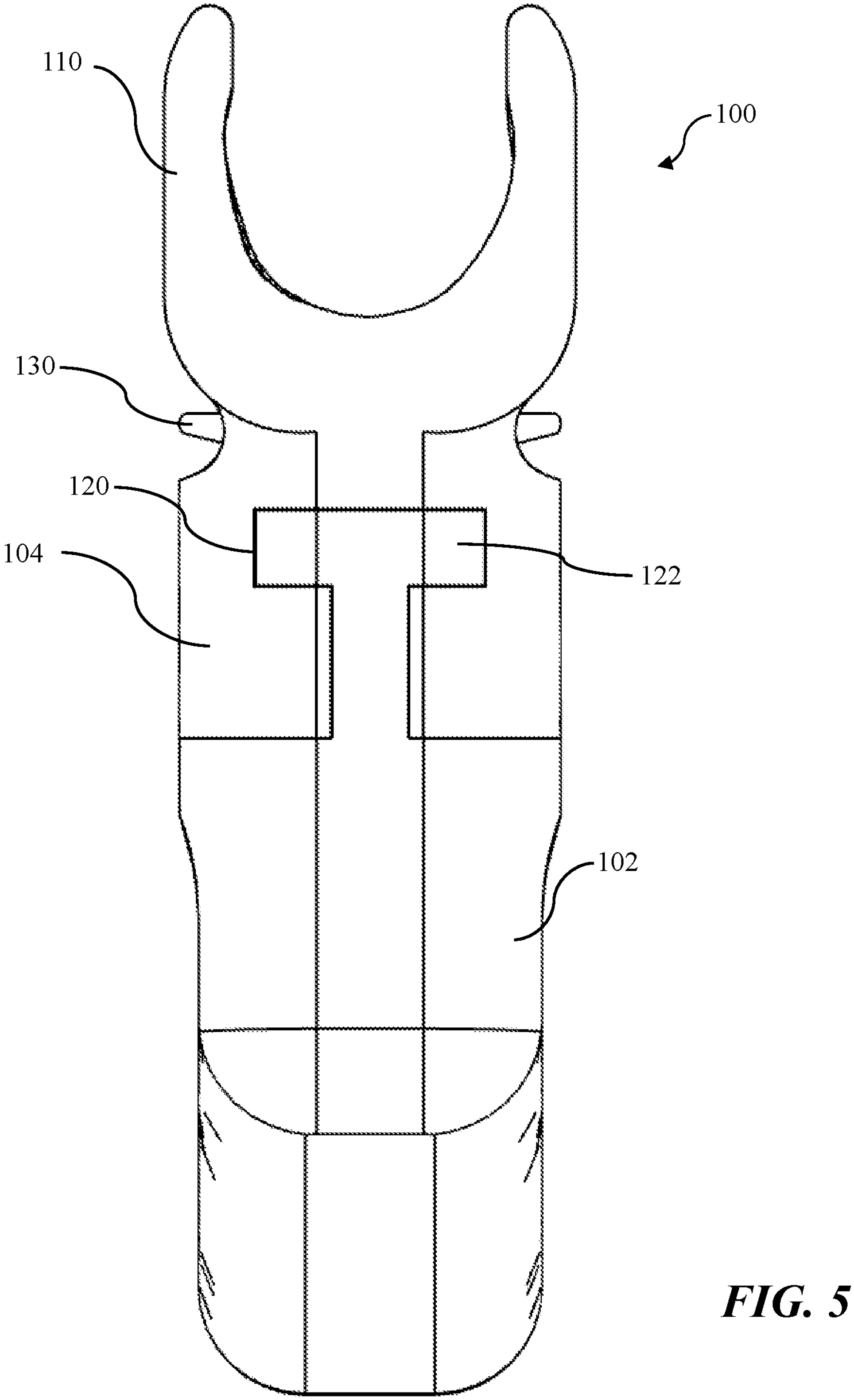
FIG. 5 is a front elevational view of the ergonomic ultrasound handle device from FIG. 1.
Figure 6:
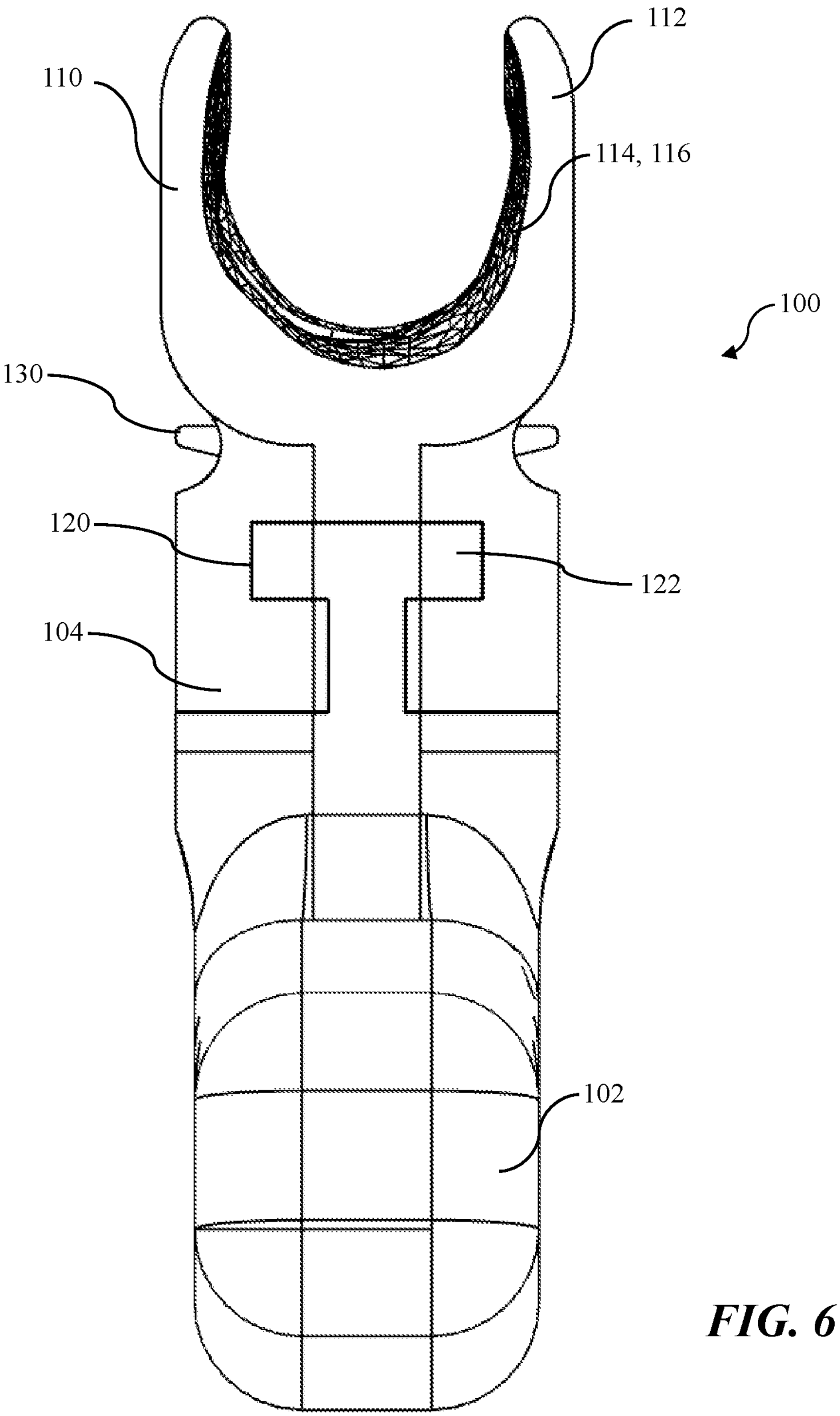
FIG. 6 is a rear elevational view of the ergonomic ultrasound handle device from FIG. 1.

The handle body 102 as shown in FIGS. 1-2 can be formed as a single unit or as multiple parts. The handle body 102 can be ergonomically designed to have a length that enables the user to be at an acceptable distance from the ultrasound transducer to position the user in a safe position. Further, the handle body 102 can be angled, as shown in FIG. 2, to allow the user to maintain the transducer in an ergonomic position during use. The angle of the handle body 102 can be adapted and modified as needed by one of skill in the art. Alternatively, the handle body 102 can include padding (not shown). This padding can be made as a single unit with the handle body 102 or can be included as an attachment to the handle body 102.

The clamp body 104 can include a top end 106 and a bottom end 108. The top end 106 can include a clip 110 formed thereon for maintaining the ultrasound transducer in engagement with the handle body 102. In certain embodiments, the clip 110 can include a plurality of clips 110. The clip 110 can be formed to engage a specific ultrasound transducer. In other embodiments, the clip 110 can be configured as a universal handle body for attaching to multiple types of ultrasound transducers. The handle body 102 and the clamp body 104 can be manufactured from a material that can be non-reactive, biocompatible, and sanitizable. For example, the handle body 102 and the clamp body 104 can be formed of the same material, including various polymers, composites, and other materials compatible with ultrasound devices, examples of which are well known to those of skill in the art. Alternatively, the clamp body 104 can be formed of a different material from that of the handle body 102.

The clips 110 can be shaped to engage the handle of an ultrasound transducer. The clips 110 can be formed to allow the ergonomic ultrasound handle device 100 to be removably attached to the handle of an ultrasound transducer. This engagement can enable the ergonomic ultrasound handle device 100 to control the positioning of the transducer, while creating a space between the handle of the transducer and the ergonomic ultrasound handle device 100. The benefit of this engagement can be to allow the user to hold the transducer in an ergonomic position. In certain embodiments, the clips 110 can include spring fit arms 112 to engage sides of the transducer handle and hold the transducer handle in place. A skilled artisan can select other suitable clips 110 for retaining the transducer handle, as desired.

The spring fit arms 112 can include an inner surface 114 that receives the transducer handle, in operation. The inner surface 114 can include a gripping material, textured material, or an otherwise textured surface 116 that can grippingly engage the transducer handle. The spring fit arms 112 and the textured surface of the clips 110 can militate against the transducer handle slipping undesirably from the ergonomic ultrasound handle device 100, in operation.

More specifically, the clips 110 can be shaped to fit a specific brand of transducer. In other words, the inner surface 114 of the clips 110 can be configured to be complementary or specifically mate with one or more portions of the handle shape of a specific brand of transducer. For example, as shown in FIG. 1, the inner surface 114 of one of the clips 110 includes a cutout 118. The cutout 118 can be complementary to a portion of a specific transducer handle. Alternatively, the clips 110 can be formed to enable engagement with any ultrasound transducer, thereby enabling the clips 110 to engage with the handle of any transducer handle.

It should be appreciated that where the clamp body 104 is removably connected to the handle body 102, a user can selectively place a specific clamp body 104 configured to receive the desired transducer. Accordingly, the user can utilize a single handle body 102 across multiple transducer handles. Further, the user can easily remove the clamp body for disposal, as needed. This allows the user to specifically select the clamp body 104 designed to best engage the handle of the transducer. It also enables the clamp body 104 to be sanitized separately from the handle body 102.

Figure 7:
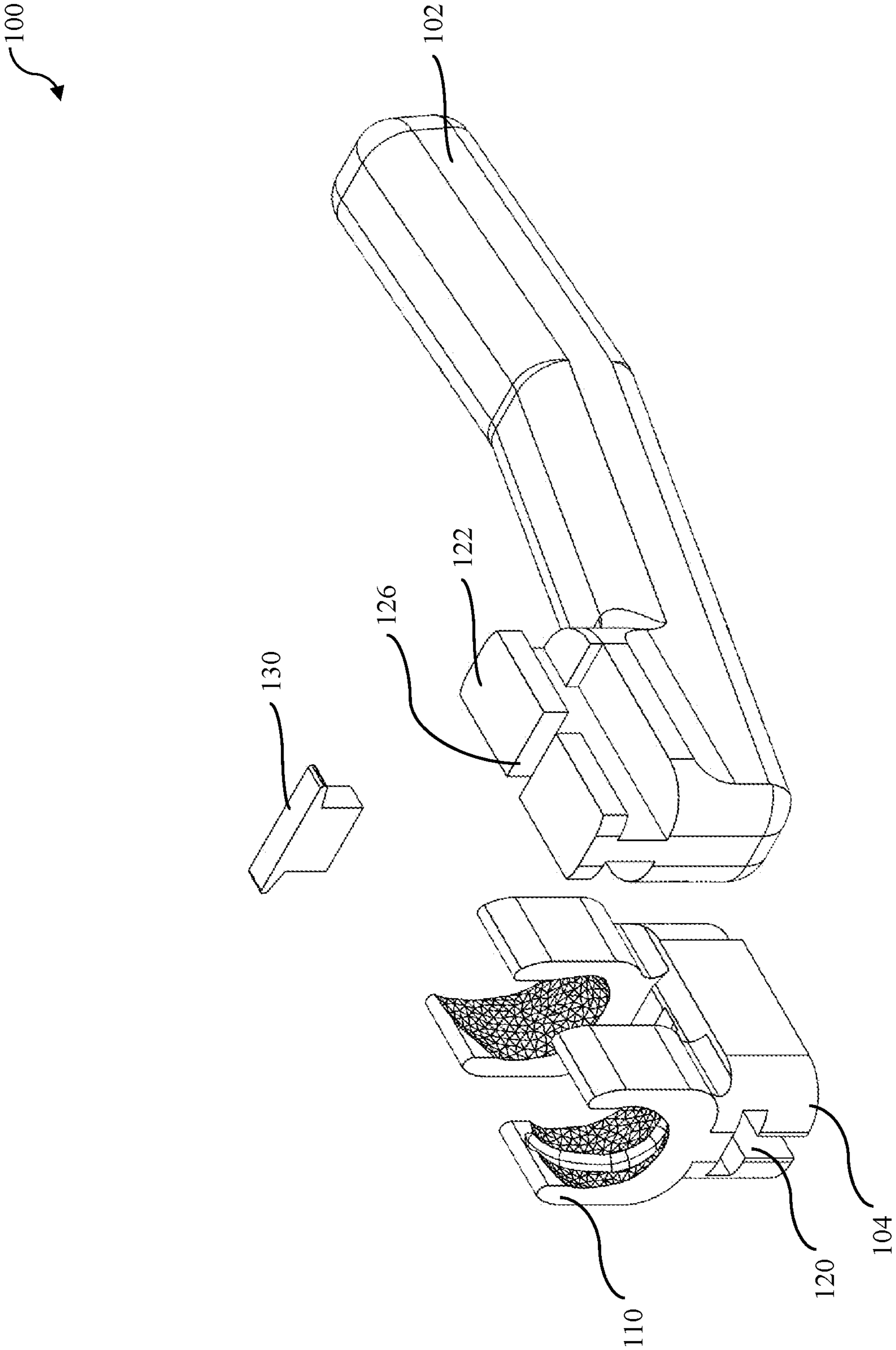
FIG. 7 is an exploded, top perspective view of an ergonomic ultrasound handle device of FIG. 1.
Figure 8:
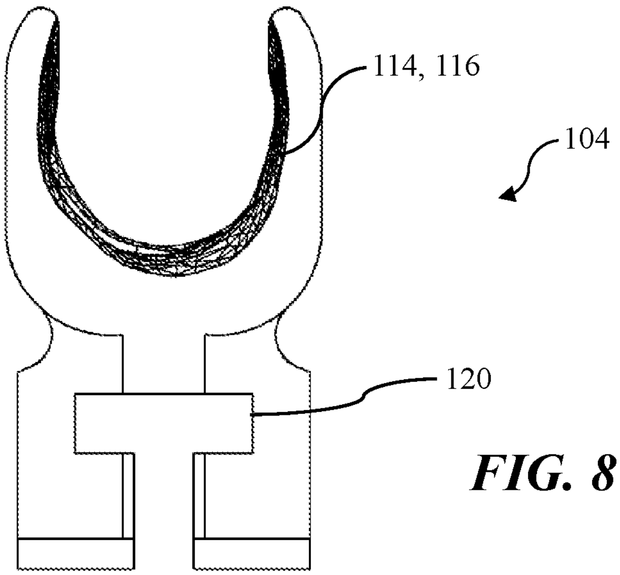
FIG. 8 is a front elevational view of a clamp body of the ergonomic ultrasound handle device from FIG. 1.
Figure 9:
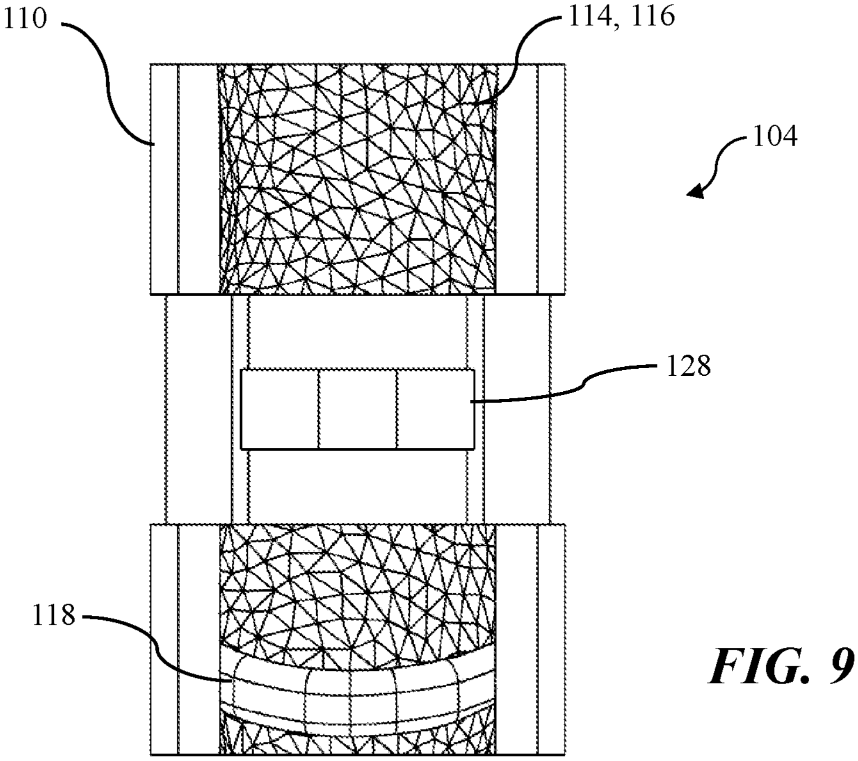
FIG. 9 is a top plan view of a clamp body of the ergonomic ultrasound handle device from FIG. 8.

As shown in FIG. 7-8, a channel 120 can be formed in the bottom end 108 of the clamp body 104 to securely attach the clamp body 104 to the handle body 102. A projection 122 can be disposed on and extends outwardly from the handle body 102. A shape of the projection 122 can correspond to a shape of the channel 120 of the clamp body 104, such that the channel 120 removably, slidably receives the projection 122. In some embodiments, each of the channel 120 and the projection 122 can be substantially T-shaped, however other shapes can also be used without departing from the spirit of the present disclosure. Advantageously, the channel 120 and the projection 122 connection can allow the clamp body 104 to be secured to the handle body 102, in operation. In particular, the T-shape can militate against the clamp body 104 to undesirably separate from the handle body 102. While specific shapes are disclosed herein, a skilled artisan can select other suitable shapes within the scope of the present disclosure.

To further secure the clamp body 104 to the handle body 102, the ergonomic ultrasound handle device 100 can include a locking mechanism 124. The locking mechanism 124 can include a gap 126 formed through the projection 122 of the handle body 102, an opening 128 formed in the clamp body 104, and a locking tab 130. The opening 128 in the clamp body 104 can be formed to align with the gap 126 of the projection 122 of the handle body 102 when the clamp body 104 is disposed on the handle body 102. The locking tab 130 can be removably disposed through the opening 128 of the clamp body 102 and the gap 126 of the projection 122 of the handle body 102 when the clamp body 104 is disposed on the handle body 102. In some embodiments, the locking tab 130 can be substantially T-shaped, however other shapes can also be used without departing from the spirit of the present disclosure. Advantageously, the T-shape of the locking tab 130 can hold the locking tab 130 within the top end 106 of the clamp body 102 while still engaging with the gap 126 and the opening 128. It should be appreciated that the locking mechanism 124 can militate against the clamp body 104 undesirable sliding from the handle body 102, in operation, but still allowing for the user to easily disengage the locking mechanism 124 to remove the clamp body 102, as desired.

Figure 10:
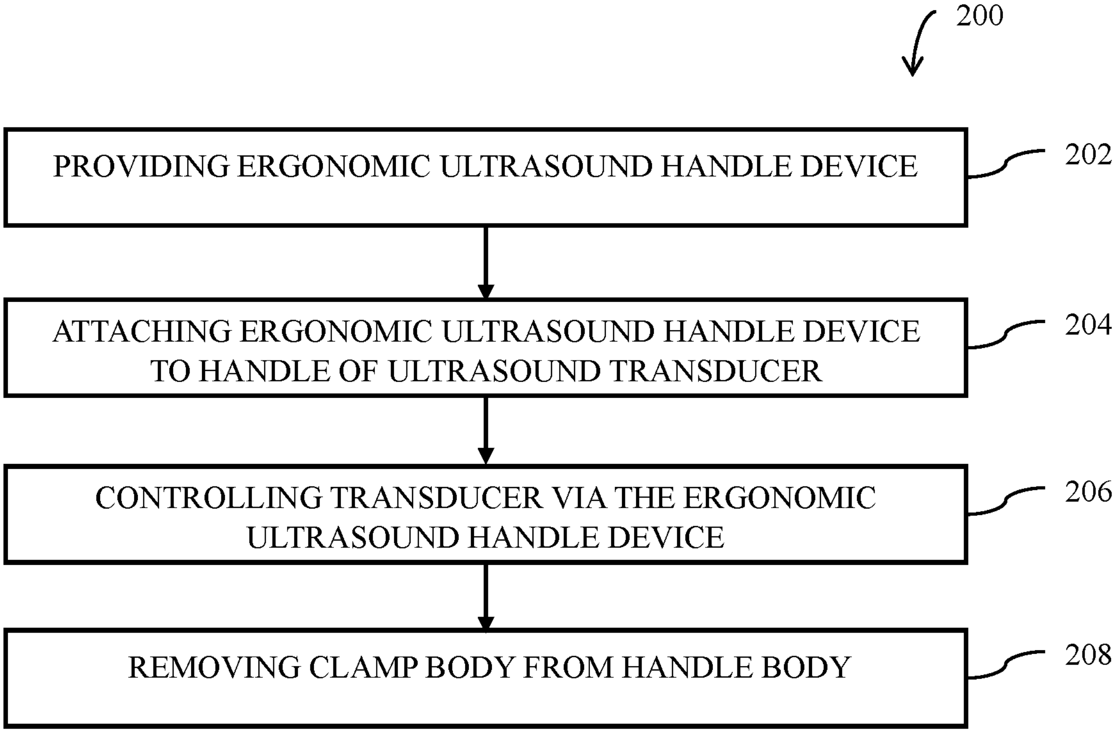
FIG. 10 is a flow chart depicting a method of ergonomically controlling an ultrasound transducer.

The present disclosure further contemplates a method 200 of ergonomically controlling an ultrasound transducer, for example, as shown in FIG. 10. The method 200 can include a step 202 of providing the ergonomic ultrasound handle device 100, as described herein. A step 204 of the method 200 can include removably attaching the ergonomic ultrasound handle device 100 to the handle of an ultrasound transducer via the clips 110. The method 200 can include a step 206 of controlling the ultrasound transducer by applying pressure and motion to the ergonomic ultrasound handle device 100, whereby the handle transmits the motion and pressure to the transducer. The method 200 can include a further step 208 of removing the clamp body 104 from the handle body 102, thereby allowing the user to dispose of the clamp body 104 and clean the handle body 102.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments can be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. An ergonomic ultrasound handle device comprising:

a handle body including a projection disposed on and extending outwardly from the handle body, the projection including a gap formed therein; and a clamp body removably, slidably coupled to the handle body for engaging an ultrasound transducer, the clamp body including a top end and a bottom end, with a clip disposed on the top end of the clamp body for maintaining the ultrasound transducer in engagement with the handle body, a channel formed in the bottom end of the clamp body, the channel corresponding to the projection of the handle body and removably, slidably receiving the projection of the handle body, a locking mechanism, and an opening formed therethrough, wherein each of the channel and the projection are substantially T shaped, wherein the opening in the clamp body is formed to align with the gap of the projection of the handle body when the clamp body is disposed on the handle body, wherein the locking mechanism further includes a locking tab removably disposed through the opening of the clamp body and the gap of the projection of the handle body when the clamp body is disposed on the handle body.

2. The device of claim 1, wherein the locking tab is substantially T shaped.

3. The device of claim 1, wherein the clamp body is formed as a single unit with the handle body.

4. The device of claim 1, wherein the clip includes a plurality of clips.

5. The device of claim 1, wherein the clip is formed to engage a specific ultrasound transducer.

6. The device of claim 1, wherein the handle body is configured as a universal handle body for attaching to multiple types of ultrasound transducers.

7. The device of claim 1, wherein the clip includes spring fit arms to engage sides of the transducer handle and hold the transducer handle in place.

8. The device of claim 7, wherein an inner surface of the arms includes a gripping material, texture material, or textured surface that can grippingly engage the transducer handle.

9. The device of claim 1, wherein the handle body and the clamp body are manufactured from a material that is non-reactive, biocompatible, and sanitizable.

10. A method of ergonomically controlling an ultrasound transducer, comprising:

providing an ergonomic ultrasound handle device including a handle body including a projection disposed on and extending outwardly from the handle body, the projection including a gap formed therein; and a clamp body removably, slidably coupled to the handle body for engaging the ultrasound transducer, the clamp body including a top end and a bottom end, with a clip disposed on the top end of the clamp body for maintaining the ultrasound transducer in engagement with the handle body, a channel formed in the bottom end of the clamp body, the channel corresponding to the projection of the handle body and removably, slidably receiving the projection of the handle body, a locking mechanism, and an opening formed therethrough, wherein each of the channel and the projection are substantially T shaped, wherein the opening in the clamp body is formed to align with the gap of the projection of the handle body when the clamp body is disposed on the handle body, wherein the locking mechanism further includes a locking tab removably disposed through the opening of the clamp body and the gap of the projection of the handle body when the clamp body is disposed on the handle body;

removably attaching the ergonomic ultrasound handle device to the ultrasound transducer; and controlling the ultrasound transducer by applying pressure and motion to the handle body, whereby the handle body transmits the motion and pressure to the ultrasound transducer.

11. The method of claim 10, further comprising a step of removing the clamp body after the step of controlling the ultrasound transducer by applying pressure and motion to the handle body.

* * * * *